Figure 1:
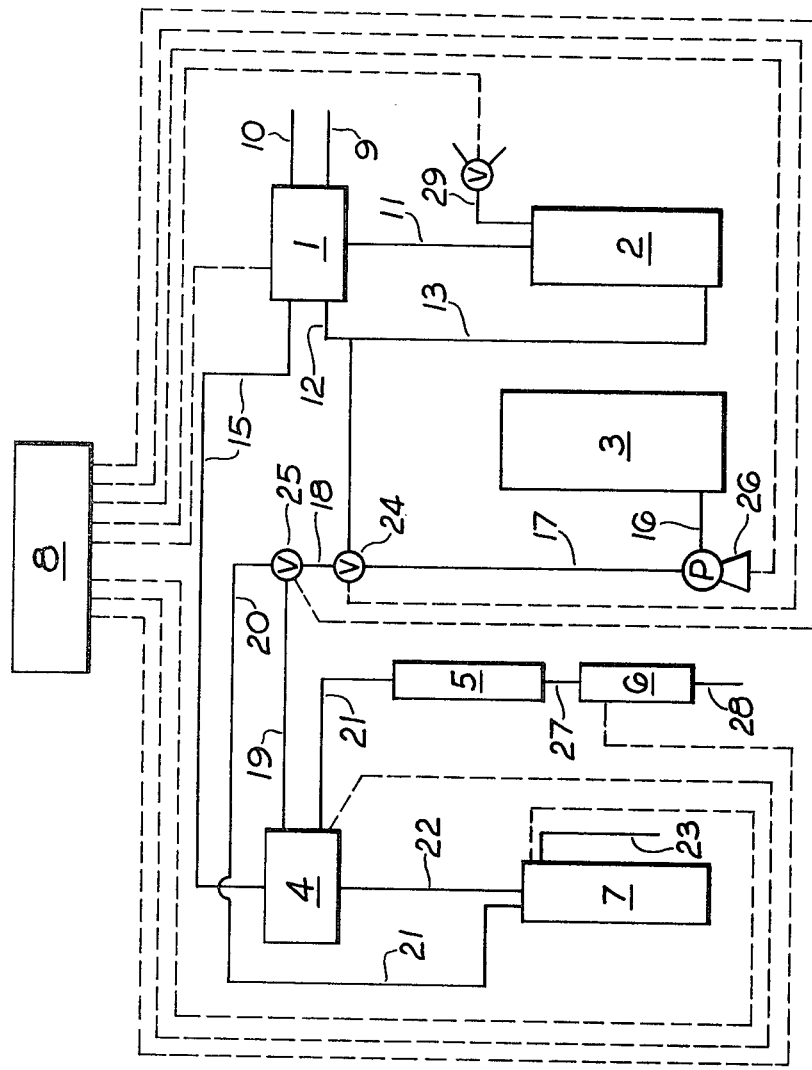

United States Patent [19]

Hulme et al.

[11] 4,258,564
[45] Mar. 31, 1981

[54] POLYMER CHARACTERIZATION APPARATUS

[75] Inventors: Joseph M. Hulme; William E. Thibodeau, both of Sarnia, Canada

[73] Assignee: Polysar Limited, Sarnia, Canada

[21] Appl. No.: 101,016

[22] Filed: Dec. 6, 1979

[30] Foreign Application Priority Data

Mar. 28, 1979 [CA] Canada ................................. 324302

[51] Int. Cl.³ ............................................ G01N 11/00
[52] U.S. Cl. .................................. 73/61.1 C; 73/61 R
[58] Field of Search .............. 73/61.1 C, 55, 53, 61 R; 210/31 C, 198 C; 422/70

[56] References Cited

U.S. PATENT DOCUMENTS

| 3,556,730 | 1/1971 | Mitacek ................................. 23/230 |
| 4,095,472 | 6/1978 | Mowery, Jr. ................... 73/422 GC |

Primary Examiner—John Petrakes
Assistant Examiner—Joseph W. Roskos
Attorney, Agent, or Firm—Stevens, Davis, Miller & Mosher

[57] ABSTRACT

An apparatus and a method of operating the apparatus are provided for obtaining a sample of polymer cement and for determining the polymer content of the cement and a molecular weight of the polymer. The apparatus comprises a valve means in combination with a dilution means whereby dilute polymer solution is supplied to a solution viscometer means and to a gel permeation chromatographic means. Operation of the apparatus is controlled by a micro computer. The apparatus and method are useful for determining the polymer content and polymer molecular weight of, for example, polybutadiene formed in a polymerization reactor.

8 Claims, 8 Drawing Figures

POLYMER CHARACTERIZATION APPARATUS

This invention relates to an apparatus for obtaining a sample of the contents of a polymerization reactor and to a method for determining the polymer content of the sample and a molecular weight of the polymer.

In the field of polymerization of hydrocarbyl monomers it is necessary to control various parameters of the polymerization in order to obtain a polymer of desired specific properties. One of the many polymer properties which has to be controlled is molecular weight and a method for more rapidly permitting the determination of the molecular weight leads to an improvement in the degree of control that can be exercised over the polymerization. One of the other properties which has to be controlled is the conversion of monomer or monomers to polymer. When a polymerization is undertaken in one or more hydrocarbon diluents and the polymer is soluble in the diluent as it is formed in the reactor or series of reactors, the solution of the polymer in the diluent is known as a cement; the polymer content of the cement is the measure of the conversion of monomer to polymer. The cement from the polymerization system is treated to remove the diluent and yield the polymer for packaging and shipment. Efficient control of the polymerization process means that the polymer will meet the various desired specific properties.

Accordingly, one object of the invention is to provide an apparatus for obtaining a sample of the contents of a polymerization reactor and for determining the polymer content of the sample and a molecular weight of the polymer, the polymer sample being a solution of the polymer in one or more hydrocarbon diluents. A second object of the invention is to provide a method for determining the polymer content and a molecular weight of the polymer of a sample of the polymer dissolved in one or more hydrocarbon diluents as obtained from a polymerization reactor.

In accordance with the invention, there is provided an apparatus for obtaining from a polymerization reactor a sample of polymer dissolved in one or more hydrocarbon diluents and for determining the polymer content of said sample and a molecular weight of said polymer, which apparatus comprises:

(a) polymerization reactor means,
(b) line for removing from said reactor means a polymeric product dissolved in one or more hydrocarbon polymerization diluents,
(c) valve means for the removal from said line of an essentially constant volume sample of said polymeric product dissolved in said diluent,
(d) means for storing hydrocarbyl solvent,
(e) dilution means for adding hydrocarbyl solvent to and mixing said hydrocarbyl solvent with said essentially constant volume sample to provide an essentially constant volume of dilute polymer solution,
(f) line for transferring said dilute polymer solution to a selector valve,
(g) a first line from said selector valve for transferring a constant volume of said dilute polymer solution to a solution viscometer means which is maintained at an essentially constant temperature,
(h) line for transferring hydrocarbyl solvent to said solution viscometer means,
(i) a second line from said selector valve for transferring a constant volume of said dilute polymer solution to one or more gel permeation chromatographic columns,
(j) line for transferring hydrocarbyl solvent to said one or more gel permeation chromatographic columns,
(k) means for causing said dilute polymer solution to flow through a capillary in said solution viscometer means and to activate a timing device to determine and record the flow time for the flow through said capillary of a constant volume of said dilute polymer solution,
(l) means for causing said hydrocarbyl solvent to flow through a capillary in said solution viscometer means and to activate a timing device to determine and record the flow time for the flow through said capillary of a constant volume of said hydrocarbyl solvent,
(m) means for causing the flow through said one or more gel permeation chromatographic columns of hydrocarbyl solvent at an essentially constant rate of flow,
(n) means for determining and recording the refractive index difference as a function of time for the effluent from said one or more gel permeation chromatographic columns, said refractive index difference being the difference between the refractive index of the column effluent and that of a control fluid,
(o) micro computer means programmed to control the operation of the apparatus, to determine and record said flow times from said solution viscometer means, to record said refractive index difference as a function of time and to calculate from said refractive index difference the polymer content of said sample and from said flow times and polymer content a molecular weight of said polymer, and
(p) recorder/display means for providing the data calculated in (o).

There is also provided an apparatus for obtaining from a polymerization reactor a sample of polymer dissolved in one or more hydrocarbon diluents and for determining the polymer content of said sample and a molecular weight of said polymer, which apparatus comprises:

(a) polymerization reactor means,
(b) line for removing from said reactor means a polymeric product dissolved in one or more hydrocarbon polymerization diluents,
(c) valve means for the removal from said line of an essentially constant volume sample of said polymeric product dissolved in said diluent,
(d) a first means for storing a first hydrocarbyl solvent,
(e) a second means for storing a second hydrocarbyl solvent,
(f) dilution means for adding and mixing said first hydrocarbyl solvent with said essentially constant volume sample to provide an essentially constant volume of dilute polymer solution,
(g) line for transferring said dilute polymer solution to a selector valve,
(h) a first line from said selector valve for transferring a constant volume of said dilute polymer solution to a solution viscometer means which is maintained at an essentially constant temperature,
(i) a line for transferring said first hydrocarbyl solvent to said solution viscometer means,
(j) a second line from said selector valve for transferring a constant volume of said dilute polymer solution to one or more gel permeation chromatographic columns, (k) a line for transferring said second hydrocarbyl solvent to said gel permeation chromatographic columns, (l) means for causing said dilute polymer solution to flow through a capillary in said solution viscometer means and to activate a timing device to determine and record the flow time for the flow through said capillary of a constant volume of said dilute polymer solution, (m) means for causing said first hydrocarbyl solvent to flow through said capillary in said solution viscometer means and to activate a timing device to determine and record the flow time for the flow through said capillary of a constant volume of said solvent, (n) means for causing the flow through said one or more gel permeation chromatographic columns of said second hydrocarbyl solvent at an essentially constant rate of flow.

(o) means for determining and recording the refractive index difference as a function of time for the effluent from said one or more gel permeation chromatographic columns, said refractive index difference being the difference between the refractive index of the column effluent and that of a control fluid, (p) micro computer means programmed to control the operation of the apparatus, to determine and record said flow times from said solution viscometer means, to record said refractive index difference as a function of time and to calculate from said refractive index difference the polymer content of said sample and from said flow times and polymer content a molecular weight of said polymer, and (q) recorder/display means for providing the data calculated in (p).

Also in accordance with the invention, there is provided a method for determining for a sample of a polymer dissolved in one or more hydrocarbon diluents and obtained from a polymerization reactor the polymer content and a molecular weight of said polymer which method comprises:

(a) transferring an essentially constant volume of said sample to a dilution means and adding to and mixing with said sample a hydrocarbyl solvent to provide an essentially constant volume of dilute polymer solution.

(b) transferring said dilute polymer solution to a selector valve, (c) transferring from said selector valve a constant volume of said dilute polymer solution to a solution viscometer means maintained at an essentially constant temperature.

(d) transferring from said selector valve a constant volume of said dilute polymer solution to one or more gel permeation chromatographic columns, (e) causing said dilute polymer solution to flow through a capillary in said solution viscometer means and causing the activation of a timing device to determine and record the flow time for a constant volume of said dilute polymer solution to flow through said capillary, (f) transferring hydrocarbyl solvent to said solution viscometer means, causing said hydrocarbyl solvent to flow through said capillary and causing the activation of a timing device to determine and record the flow time for a constant volume of said hydrocarbyl solvent to flow through said capillary, (g) causing the flow through said one or more gel permeation chromatographic columns of hydrocarbyl solvent at an essentially constant rate of flow and causing the determining and recording of the refractive index difference as a function of time for the effluent from said one or more columns, said refractive index difference being the difference between the refractive index of the column effluent and that of a control fluid, (h) causing a micro computer means to direct the transfers and flows to take place, to determine and record the flow times through the capillary of the solution viscometer means, to record the refractive index difference as a function of time, to calculate from said refractive index difference the polymer content of said sample, to calculate from said polymer content and from said flow times a molecular weight of the polymer and to cause a recorder/display means to provide the data calculated.

There is also provided a method for determining for a sample of polymer dissolved in one or more hydrocarbon diluents and obtained from a polymerization reactor the polymer content and a molecular weight of said polymer, which method comprises:

(a) transferring an essentially constant volume of said sample to a dilution means and adding to and mixing with said sample a first hydrocarbyl solvent to provide an essentially constant volume of dilute polymer solution, (b) transferring said dilute polymer solution to a selector valve, (c) transferring from said selector valve a constant volume of said dilute polymer solution to a solution viscometer means maintained at an essentially constant temperature, (d) transferring from said selector valve a constant volume of said dilute polymer solution to one or more gel permeation chromatographic columns, (e) causing said dilute polymer solution to flow through a capillary in said solution viscometer means and causing the activation of a timing device to determine and record the flow time for a constant volume of said dilute polymer solution through said capillary, (f) transferring said first hydrocarbyl solvent to said solution viscometer means, causing said solvent to flow through said capillary and causing the activator of a timing device to determine and record the flow time for a constant volume of said solvent to flow through said capillary, (g) causing the flow through said one or more gel permeation chromatographic columns of a second hydrocarbyl solvent at an essentially constant rate of flow and causing the determining and recording of the refractive index difference as a function of time for the effluent from said one or more columns, said refractive index difference being the difference between the viscometer means, to record the refractive index difference as a function of time, to calculate from said refractive index difference the polymer content of said sample, to calculate from said polymer content and from said flow times a molecular weight of the polymer and to cause a recorder/display means to provide the data calculated.

The apparatus and method of the invention are especially applicable to those systems in which normally solid polymers are prepared in solution. Examples of such polymers are polybutadiene, polyisoprene, ethylene-propylene and ethylene-propylene diene monomer polymers and styrene-butadiene polymers. Such polymers may be prepared by means well known in the art, including polymerization of the monomers by anionic and Ziegler-type catalyts. The hydrocarbon diluents used in the polymerization may include pentane, hexane, benzene, toluene, benzene/butene-1 mixtures, cyclohexane and mixtures thereof.

The sample obtained from the polymerization reactor may be in a metal bomb, in a glass or metal syringe or may be in a valve means capable of isolating a predetermined volume of the polymer solution. For fully automatic operation of the apparatus and method of the invention, it is necessary that the sample be obtained in such a valve means. For periodic operation of the apparatus and method of the invention, the sample may be supplied on a periodic basis from a bomb or syringe or from a valve means. A preferred valve means comprises a two-position valve having a housing equipped with ports, the chamber of said housing containing a movable two-position valve core equipped with flow channels each of which separately communicates with two adjacent ports, a first port being in communication with inlet means for polymer cement, a second port being in communication with an outlet means for said cement, a third port being in communication with a dilution means, a fourth port being in communication with the dilute polymer solution in said dilution means and a fifth port being for removal of dilute polymer solution from the valve means, a first flow channel communicating in its first position with said first and second ports and in its second position with said second and third ports and a second flow channel communicating in its first position with said third and fourth ports and in its second position with said fourth and fifth ports. Preferred valve means are described hereinafter.

The dilution means comprises a wide diameter closed cylindrical chamber, a means for transferring an essentially constant volume of the sample into the chamber, a means for transferring hydrocarbyl solvent into the chamber and a means of transferring dilute polymer solution out of the mixing chamber. A preferred dilution means comprises a narrow diameter cylindrical chamber connected at its upper end to the third port of said valve means and connected at its lower end to a wide diameter closed cylindrical chamber which has at the side wall at its lower end a line in communication with the fourth port of said valve means and the solvent storage means and has at its upper end a line having a valve therein whereby said line may be connected to a supply of compressed gas or to the atmosphere, said narrow diameter cylindrical chamber having located concentrically therein and axially slidably movable within a close fitting plunger equipped with seals to prevent fluid leakage and having at its lower end depending into said wide diameter chamber a flange end for abutting engagement with the under surface of the wide diameter chamber at the point where the narrow diameter cylindrical chamber is attached to the wide diameter chamber, and said wide diameter closed cylindrical chamber having concentrically located therein and axially slidably movable within a close fitting double acting barrier piston equipped with seals to prevent fluid leakage and having a stirring means located within said wide diameter chamber and below said double acting barrier piston. A preferred dilution means is described hereinafter.

Hydrocarbyl solvents suitable for dilution of said sample include benzene, toluene, cyclohexane, di-isobutylene and tetrahydrofuran. Preferred solvents are tetrahydrofuran, cyclohexane and toluene.

A selector valve for receiving and transferring the dilute polymer solution preferably is a multi-port valve suitably with six ports and constructed such that each of two adjacent ports may be connected to each other to permit fluid flow from one port to the other. A preferred selector valve is described hereinafter.

The solution viscometer means is a viscometer suitable for determining the dilute solution viscosity of a polymer solution by flow through a capillary. An Ubbelodhe type viscometer is the most preferred type. The dilute solution flows from a small reservoir through the capillary into a larger reservoir and the time is measured for a constant volume of the dilute solution to flow through the capillary—such time measurement accurate to 0.01 second, may be activated by electrical means or by having beams of light associated with light detectors as sensing mechanisms. The movement of the dilute polymer solution within the viscometer is controlled by gas pressure or by vacuum. A preferred solution viscometer means is described hereinafter.

The gel permeation chromatographic column is a column of the type well known in the art, being a metal tube of up to about 6 mm diameter containing a packing also well known in the art such as crosslinked porous polystyrene beads or silanized porous glass spheres or particles. Solvent was supplied to the column at an essentially constant rate of flow. The effluent from the column passes through a differential refractometer also containing a control fluid, the difference in refractive index between the effluent and the control fluid being determined to give the refractive index difference.

The micro computer is programmed to calculate from the refractive index difference the polymer content of the original sample and from the flow times and polymer content a molecular weight of the polymer. The results of these calculations are provided by a recorder/display means.

Figure 3:
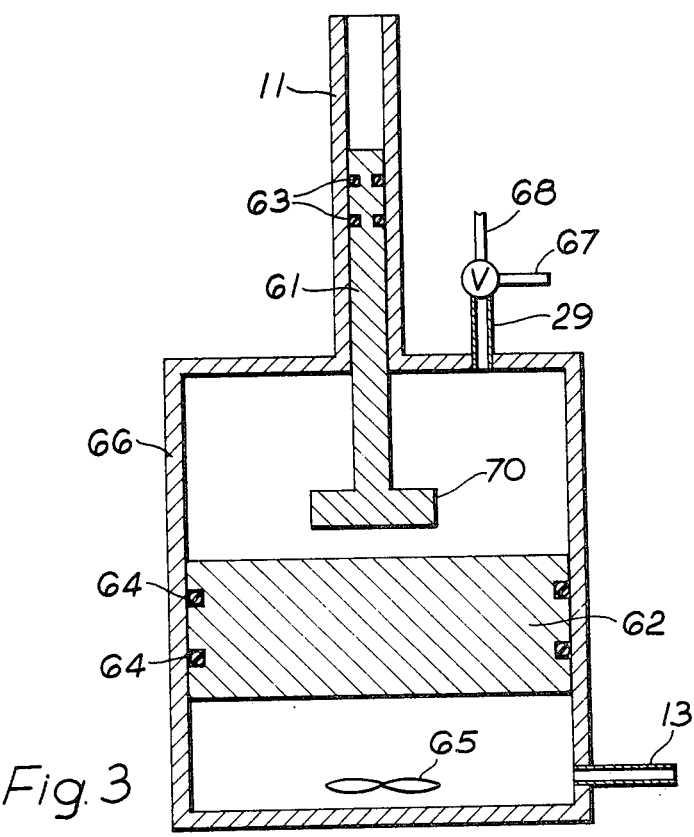
Figure 4:
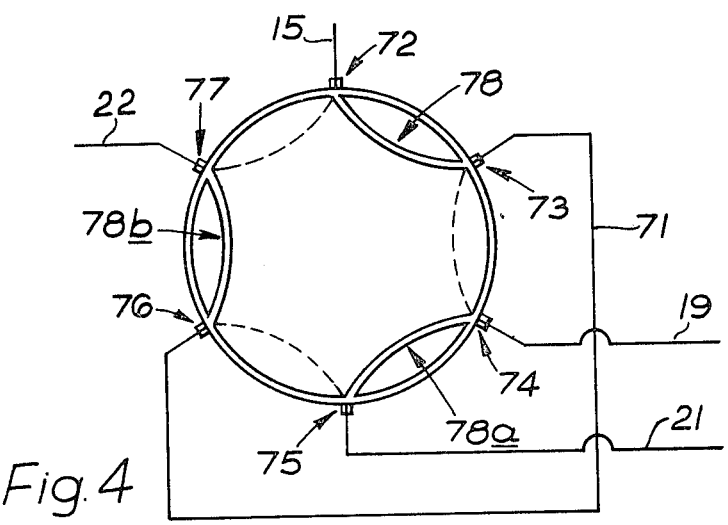
Figure 5:
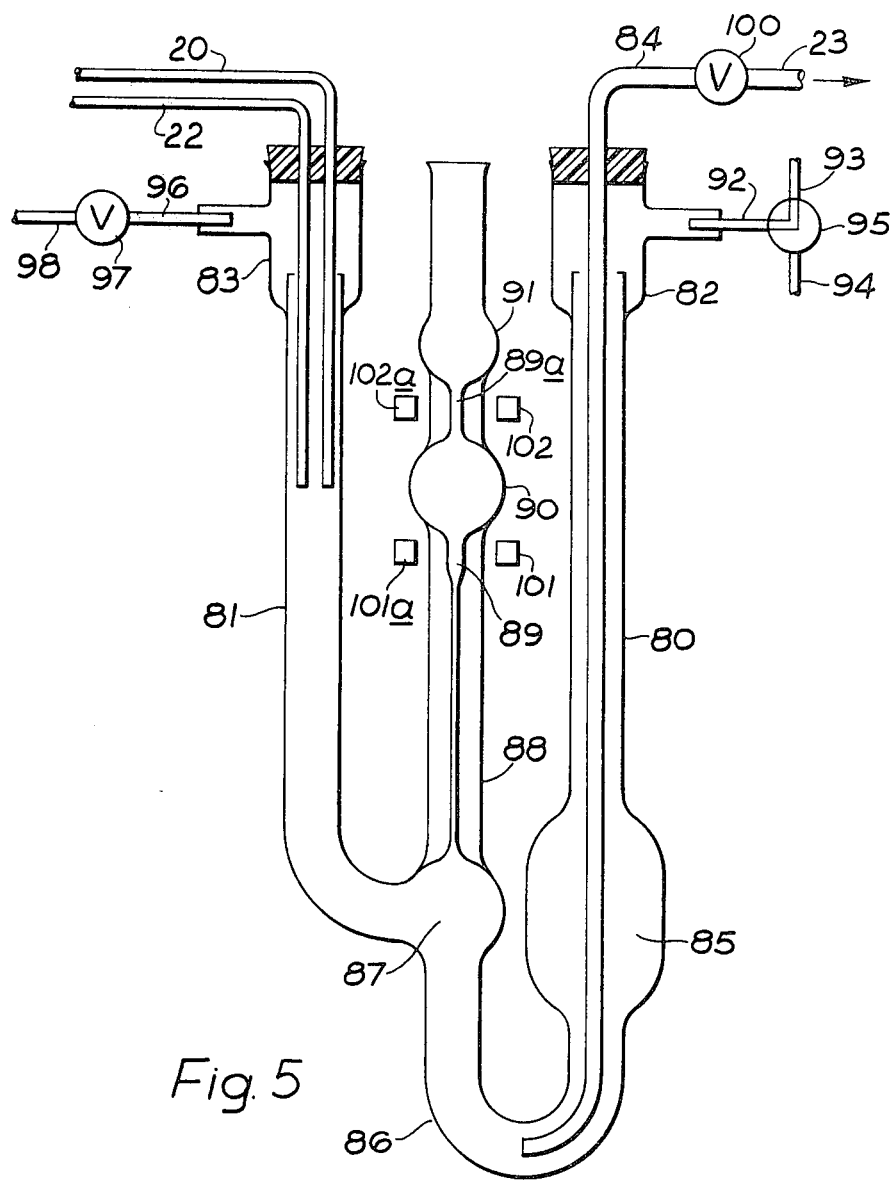
Figure 6:
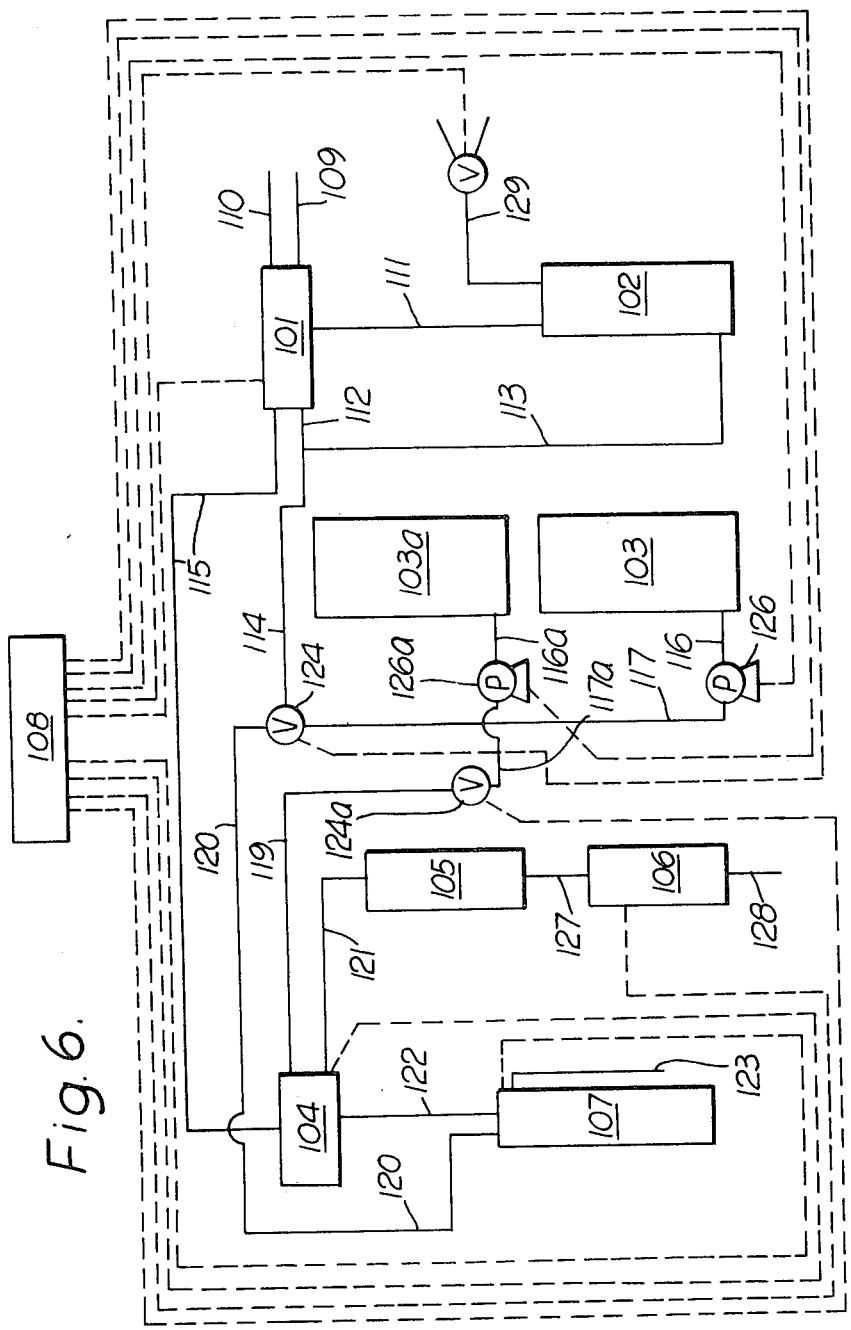

A better understanding of the invention will follow from a consideration of the drawings which describe embodiments of the invention. Referring now to the drawings, FIG. 1 is a schematic outline of an apparatus according to the invention, FIG. 2 is a schematic outline of a valve means, FIG. 2A is a detailed drawing of a suitable valve means, FIG. 2B is a detailed drawing of a suitable valve means for use on a continuous cement sampling facility, FIG. 3 is a suitable dilution means, FIG. 4 is a schematic outline of a selector valve, FIG. 5 is a suitable solution viscometer means, and FIG. 6 is a schematic outline of a further apparatus according to the invention.

With reference to FIG. 1, 1 is a multiport valve means for control of the flow of cement into the apparatus. Cement flows into the valve means by line 9 and may be directed out of the valve means by line 10 or may be directed into the dilution means 2 by cylinder 11 which forms a part of the dilution means. Line 15 is for removal of the dilute polymer solution from the dilution means via line 13 to line 12 into valve means 1 and into line 15. Reservoir 3 provides storage for the hydrocarbyl solvent, the flow of which is controlled by pump 26. Solvent may be pumped from reservoir 3 through line 16 and pump 26 to line 17 and to valve 24 which directs the flow of solvent to either of lines 14 or 18. From line 14 the solvent flows to line 13 and into the dilution means. From line 18 the solvent flows to valve 25 which directs the flow to either of lines 19 or 20. The dilute polymer solution in line 15 is fed to selector valve 4 which directs a constant volume of the dilute polymer solution by line 22 to a solution viscometer means 7 and directs a second constant volume of dilute polymer solution by line 21 to one or more gel permeation chromatographic columns 5. Hydrocarbyl solvent from line 19 is directed by selector valve 4 into line 21 and thence to flow through the one or more gel permeation chromatographic columns. The effluent from the gel permeation chromatographic columns flows by line 27 through a differential refractometer 6 and to waste disposal by line 28. Hydrocarbyl solvent from line 20 is supplied to the solution viscometer means 7 and to waste disposal by line 23. Line 29 connects the dilution means to a source of compressed gas or to atmospheric pressure. Micro computer means 8 controls the operation of the apparatus, determines and records flow times from the solution viscometer means, records from the differential refractometer refractive index differences as a function of time and calculates the polymer content of the cement and a molecular weight of the polymer. Connections from the micro computer are shown by dashed lines.

Figure 2:
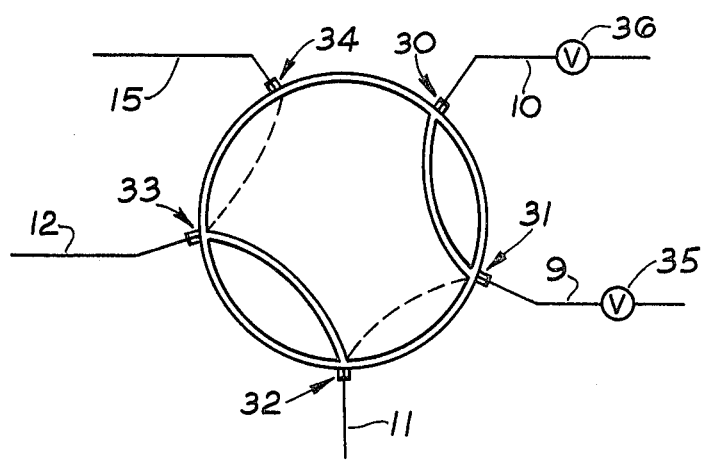

FIG. 2 is a schematic diagram of a valve means for use as valve means 1 of FIG. 1. The valve means is a two-position valve with a housing equipped with 5 ports 30, 31, 32, 33 and 34 spaced at about 72° intervals around the housing, the chamber of said housing containing a movable two-position valve core rotatable through about 72°. The valve core contains two flow channels. In a first position of said valve core, a first such flow channel is shown connecting ports 30 and 31 and the second such flow channel is shown connecting ports 32 and 33. On rotation of the valve core through about 72° to its second position, the first flow channel connects port 31 to port 32 and the second flow channel connects port 33 to port 34, as is shown by the dotted lines. Line 9 connected to port 31 supplies the cement to the valve means and line 10 connected to port 30 is for removal of excess cement, the flow of cement being through the first flow channel of the valve core as shown in the figure. Valves 35 and 36 control the flow of cement in lines 9 and 10 respectively. Connected to port 32 is cylinder 11 which is a part of the dilution means. Line 12 is for transfer of the sample and for transfer of the dilute polymer solution from the dilution means into port 33 and through the second flow channel in the second position of the valve core (as shown by the dotted line) to port 34 and out of the valve means by line 15. It will be readily apparent to one of average skill in the art that a variety of valve means may be utilized, including two-position valves with rotatable cores and two-position valves with axially movable cores.

Figures 2A, 2B:
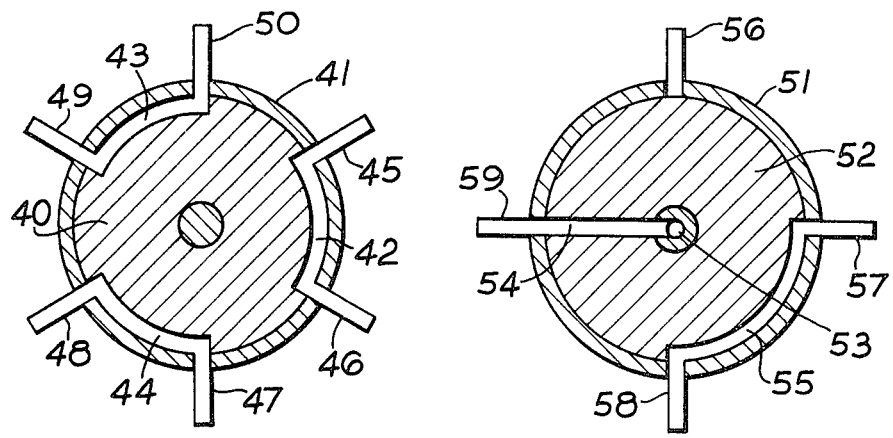

FIG. 2a is a detailed drawing of a suitable valve means 1 of FIG. 1. The valve means is a two-position valve which comprises a housing 41 equipped with six ports spaced at intervals of about 60° and a valve core 40 rotatable through about 60°. To the housing there are attached at each of the six ports lines 45, 46, 47, 48, 49 and 50. The valve core contains three flow channels 42, 43 and 44. The Figure shows line 45 (which may correspond to line 10 of FIG. 2) connected by flow channel 42 to line 46 (which may correspond to line 9 of FIG. 2). Similarly, line 47 (which may correspond to cylinder 11 of FIG. 2) is shown connected by flow channel 44 to line 48 (which may correspond to line 12 of FIG. 2) and line 49 (which may correspond to line 15 of FIG. 2) is shown connected by flow channel 43 to line 50, which is a spare line not necessary to the operation of the apparatus. By rotation of the valve core 40 through about 60° to its second position, line 46 may be connected by flow channel 42 to line 47 and line 48 may be connected by flow channel 44 to line 49.

FIG. 2b is a detailed drawing of a suitable valve means for use on a continuous cement sampling facility. The valve means is a two-position valve which comprises a housing 51 equipped with four ports spaced at intervals of about 90° and a pneumatically operated two-position valve core 52 which is movable by rotation through about 90°. The housing 51 has attached at each of the ports lines 56, 57, 58 and 59. Perpendicular to the plane of the paper is line 53 which is attached to the valve core. The valve core contains two flow channels 54 and 55. Flow channel 54 is directly connected to line 53 (which may correspond to line 9) of FIG. 2) which is the source of supply of the cement. As shown in the Figure, flow channel 54 is connected to line 59 (which may correspond to line 10 of FIG. 2) which returns the supply of cement to the continuous flowing stream. The Figure shows line 57 connected by flow channel 55 to line 58. To obtain a sample of the cement, the valve core is rotated through about 90° to its second position to connect line 53 via flow channel 54 to line 58 (which may correspond to cylinder 11 of FIG. 2) which is part of the dilution means. On rotation of the valve core back to its first position, as shown in the Figure, the fluid sample retained in line 58 is removed through flow channel 55 and line 57 (which may correspond to line 12 of FIG. 2) to the dilution means and is mixed with solvent. The dilute polymer solution is removed from the dilution means by rotation of the valve core through about 90° to its second position so that the polymer solution passes through line 57 via flow channel 55 (which now connects lines 56 and 57) to line 56 (which may correspond to line 15 of FIG. 2) and out of the valve means.

FIG. 3 is a dilution means suitable for use in the apparatus. A narrow diameter cylinder 11, forming a narrow diameter cylindrical chamber, is attached at its upper end to the valve means (line 11 of FIGS. 1 and 2) and at its lower end to a wide diameter closed cylinder 66 with end walls and defining a wide diameter closed cylinder chamber. The narrow diameter cylinder has located concentrically therein and axially slidably within the cylindrical chamber a close fitting plunger 61 equipped with seals 63 to prevent fluid leakage and having at its lower end depending into the wide diameter cylindrical chamber a flange end 70 for abutting engagement with the under surface of the wide diameter chamber at the point where the cylinder is attached to the wide diameter chamber. The wide diameter closed cylindrical chamber has concentrically located therein and axially slidably movable within said chamber a close fitting double acting barrier piston 62, equipped with seals 64 to prevent fluid leakage, for separating the chamber into two parts and for providing drive to push the plunger 61 upwardly into cylinder 11 or to push fluid downwardly out of the chamber. The chamber is equipped with a line 29 at the upper end wall of the chamber, line 29 having a valve whereby line 29 may be connected to a supply of compressed gas from line 67 to push the barrier piston downwardly in the chamber or may be connected to the atmosphere by line 68 in order to vent compressed air and permit upward movement of the barrier piston. The upward movement of the barrier piston is limited by contact with flange 70 of plunger 61 in its uppermost position of abutting engagement with the under surface of the wide diameter chamber and the downward movement of the barrier piston is limited by contact with the stirring bar 65. At the lower end of the chamber and attached to a lower portion of the wall thereof is line 13 for supply of solvent and sample to the chamber and for removal of the dilute polymer solution from the chamber. Within the chamber and below the barrier piston is a stirring means which is a magnetic stirring bar 65 which is activated by an external controlled speed stirring device of known form (not shown).

In an operation of the apparatus to provide the dilute polymer solution, and with reference to FIGS. 1, 2 and 3, the micro computer means 8 causes the valve core to be set in its first position, the pump to be set in the off condition and the barrier piston of the dilution means to be at its lowest point of travel with line 29 connected to the atmosphere. The cement to be sampled is passed (FIGS. 1 and 2) through line 9 into valve means 1 and out through line 10 to flush out the lines. Micro computer means 8 causes the valve core to be rotated to its second position so that line 9 is connected by the flow channel to cylinder 11 of the dilution means. A sample of the cement flows into cylinder 11, forcing the plunger 61 therein downward until the flange end is in contact with the barrier piston 62 which is located at the lowest point of its travel within chamber 66. Micro computer means 8 causes the valve core to be rotated back to its first position, as shown in FIG. 2, valve 24 to be set to connect lines 17 and 14, and pump 26 to be activated causing the solvent to flow from the reservoir 3 through line 16, line 17, line 14 and line 13 into the bottom of the chamber of the dilution means. The flow of solvent into the chamber forces the barrier piston 62 to move upwardly within the chamber and the upward movement of the barrier piston forces the plunger 61 to move upwardly within cylinder 11 thus displacing the cement sample from cylinder 11 through the flow channel into line 12 where at the junctions of lines 12 and 14 it is mixed with and flows with the solvent through line 13 into the bottom of the dilution means. With the stirring means in the bottom of the chamber of the dilution means activated, the solvent and sample become well mixed. When the barrier piston has been displaced to its upper most point within the chamber, micro computer means 8 deactivates the pump thereby stopping the flow of solvent into the dilution means and causes the valve core to be rotated to its second position. Micro computer means 8 activates the valve in line 29 so that compressed gas is supplied to line 29 of the dilution means thus forcing the barrier piston in a downward motion causing the displacement of the dilute polymer solution from the chamber through line 13 and into line 12 to the valve means to line 15 and thence to the analytical or property measuring means. By these operations, a constant volume of the polymer cement is obtained, a constant fraction of this volume is diluted with a constant volume of hydrocarbyl solvent and is available for subsequent use. By suitable choice of the volume of cylinder 11 and of chamber 66 it is possible to achieve the extent of dilution required.

FIG. 4 is a schematic outline of a selector valve. This selector valve is essentially similar to that shown in FIG. 2a and serves to supply the dilute polymer solution to the solution viscometer and the gel permeation chromatography columns. The selector valve is a two-position valve which comprises a housing equipped with six ports spaced at intervals of about 60° and a valve core rotatable through about 60°. To the housing there are attached at each of the six ports lines 72, 73, 74, 75, 76 and 77. The valve core contains three flow channels 78, 78a and 78b. The Figure shows line 15, which supplies dilute polymer solution, connected to port 72. Flow channel 78 connects port 72 to port 73. Line 19, which supplies hydrocarbyl solvent, is connected to port 74. Flow channel 78a connects port 74 to port 75. Line 22, which supplies dilute polymer solution to the solution viscometer means, is shown connected to port 77. Flow channel 78b connects port 77 to port 76. Line 71 is an external loop connection connecting port 73 to port 76. With the valve core in its first position, as shown in the Figure, dilute polymer solution from line 15 (from the dilution means) enters port 72, passes through flow channel 78 to port 73 through line 71 to port 76 through flow channel 78b to port 77 and into line 22 to the solution viscometer means. Micro computer means 8 (FIG. 1) causes the valve core to be rotated to its second position so that flow channel 78 connects port 73 to port 74, flow channel 78a connects port 75 to port 76 and flow channel 78b connects port 77 to port 72, as shown by the dotted lines in the Figure. Valve 24 is activated by micro computer means 8 (FIG. 1) to connect line 17 to line 18, valve 25 is activated to connect line 18 to line 19 and pump 26 is activated to supply solvent from the reservoir. The solvent enters the selector valve from line 19 to port 74, flows by flow channel 78 to port 73, flows through external loop connection 71, thus displacing the dilute polymer solution retained in loop connection 71, through port 76 and flow channel 78a to port 75 and into line 21 which supplies the displaced dilute polymer solution and solvent to the one or more gel permeation chromatographic columns. The refractive index difference determined by the differential refractometer for the effluent from the gel permeation chromatographic columns is transmitted to micro computer means 8 and determines when sufficient solvent has flowed through the chromatographic columns to wash out all the polymer which thus determines when the valve core of the selector valve may be returned to its first position.

FIG. 5 is a solution viscometer means suitable for use in the apparatus. The viscometer is of the conventional Ubbelhode type modified so that it can be automatically filled and emptied and so that the flow time in the capillary can be automatically recorded. Vertical glass arms 80 and 81 are each fitted at their upper ends with T-pieces 82 and 83 respectively; lines 20 and 22 pass through T-piece 83 into the upper portion of arm 81 and supply solvent and dilute polymer solution respectively. Arm 81 is connected at its lower end to a side of bulb 87. Arm 80 is connected at its lower end to the upper end of reservoir 85, the lower end of reservoir 85 being connected to one arm of U-tube 86. The other arm of U-tube 86 is connected to the lower end of bulb 87. Line 84 passes through T-piece 82, essentially centrally shown through arm 80, reservoir 85 and one arm of U-tube 86, terminating at a bottom point of U-tube 86; line 84 is used to remove solution or solvent from the viscometer through valve 100 and line 23 to waste by applying a vacuum to line 23. Line 92, terminating in valve 95, is connected to the side arm of T-piece 82. Lines 93 and 94 are also connected to valve 95. Line 93 is connected to a supply of compressed gas, preferably at a pressure of from about 0.025 to about 0.05 kg/cm$^2$, which may then be connected through valve 95 to line 92 to supply the motive force for moving solution or solvent within the viscometer. Line 94 is open to the atmosphere and when connected through valve 95 to line 92 allows arm 80 of the viscometer to be at atmospheric pressure. Line 98, which is open to the atmosphere, is connected through valve 97 to line 96 to the side arm of T-piece 83. When valve 97 is open, arm 81 of the viscometer is at atmospheric pressure and when valve 97 is closed, fluid may be moved within the viscometer by applying gas pressure to line 93. To the upper end of bulb 87 is attached, in the same plane as arms 80 and 81, the lower end of the capillary 88 to the upper end of which is attached a short length of wider bore tube 89 leading into bulb 90 which in turn is connected at its upper end to wider bore tube 89a which leads into bulb 91 which is equipped with a terminal open-ended tube. Light emission means 101 and 102 and light detection means 101a and 102a are fitted about tubes 89 and 89a; the beam of light from the light emission means is passed through the tube and detected on the diametrically opposite side of the tube by the light detection means. The whole viscometer is in a constant temperature bath, such as a water bath, controlled to a temperature of ±0.1° C. at a temperature within the range of 20°–30°.

When a fluid is flowing through tube 89 or tube 89a the beam of light from the respective light emission means is deflected from the light detector means and therefore is no longer detectable. Dilute polymer solution or solvent flows from bulb 91 down through capillary 88 into bulb 87, U-tube 86 and reservoir 85. At the instant when the solution or solvent flows past the point in tube 89a defined by the light beam from light emission means 102 the light beam is immediately detected by light detection means 102a—this detection of light by light detection means 102a is communicated to micro computer means 8 to initiate the operation of a timing device. The solution or solvent continues to flow through capillary 88 and at the instant when the solution or solvent flows past the point in tube 89 defined by the light beam from light emission means 101 the light beam is immediately detected by light detection means 101a—this detection of light by light detection means 101a is communicated to micro computer means 8 to stop the operation of said timing device. Thus the time, measured to an accuracy of 0.01 second, is determined for the flow of a constant volume of dilute polymer solution or solvent through the capillary 88, the constant volume being that from the point described by the light beam in tube 89a plus that of bulb 90 plus that to the point described by the light beam in tube 89.

In an operation of the solution viscometer means, dilute polymer solution enters by line 20, both of valves 95 and 97 being open to the atmosphere, and valve 100 being closed and is accumulated in bulb 87, U-tube 86 and reservoir 85. Valve 97 is closed, valve 100 is kept closed and valve 95 is switched to the supply of compressed gas in line 93. The compressed gas forces the polymer solution to flow from reservoir 85 and U-tube 86 to occupy the volume of bulb 87, capillary 88, tube 89, bulb 90, tube 89a and bulb 91. With valve 100 still closed, valves 95 and 97 are opened to the atmosphere which allows the polymer solution to flow back down into U-tube 86 and reservoir 87. As the solution flows down through capillary 88 the timing device is activated and de-activated as described hereinabove. When all the polymer solution has flowed back into bulb 87, U-tube 86 and reservoir 85, valves 95 and 97 are closed and valve 100 is opened, vacuum applied to line 23 and the polymer solution removed by line 84. Following the above procedure, solvent is supplied to the viscometer and the flow time for the solvent to flow through capillary 88 is determined and the solvent removed from the viscometer. By following the same procedure but without determining the flow time the viscometer may, if desired, be washed out with solvent to ensure complete removal of all of the polymer of the dilute polymer solution.

With reference to FIG. 6, an apparatus is shown which is similar to that of FIG. 1 except that a hydrocarbyl solvent is used, one solvent being for use in the solution viscometer means and the other solvent being for use in the gel permeation chromatographic columns. 101 is a multiport valve means, such as that shown in either of FIG. 2a or 2b, for control of the flow of cement into the apparatus. Cement flows into the valve means by line 109 and may be directed out of the valve means by line 110 or may be directed into the dilution means 102 by cylinder 111 which forms part of the dilution means, as shown in FIG. 3 as cylinder 11. Line 115 is for removal of the dilute polymer solution from the dilution means via line 113 to line 112 into valve means 101 and into line 115. Reservoir 103 provides storage for a first hydrocarbyl solvent, the flow of which is controlled by pump 126. Reservoir 103a provides storage for a second hydrocarbyl solvent, the flow of which is controlled by pump 126a. Solvent may be pumped from reservoir 103 through line 116 and pump 126 to line 117 and to valve 124 which directs the flow of solvent to either of lines 114 or 120. From line 114 the solvent flows to line 113 and into the dilution means. From line 120 the solvent flows into the solution viscometer means 107. Solvent may be pumped from reservoir 103a through line 116a and pump 126a to line 117a and to valve 124a which, when in the open position, allows the solvent to flow through line 119 into selector valve 104. The dilute polymer solution in line 115 is fed to selector valve 104, as shown in FIG. 4 as line 15, which directs a constant volume of the dilute polymer solution by line 122 (line 22 of FIG. 4) to the solution viscometer means 107 and directs a second constant volume of dilute polymer solution by line 121 (line 21 of FIG. 4) to one or more gel permeation chromatographic columns 105. Hydrocarbyl solvent from line 119 is directed by selector valve 104 into line 121 and thence to flow through the one or more gel permeation chromatographic columns. The effluent from the gel permeation chromatographic columns flows by line 127 through a differential refractometer 106 and to waste disposal by line 128. Hydrocarbyl solvent from line 120 is supplied to the solution viscometer means 107 and to waste disposal by line 123. Line 129 connects the dilution means to a source of compressed gas or to atmospheric pressure. Micro computer means 108 controls the operation of the apparatus, determines and records flow times from the solution viscometer means, records from the differential refractometer the refractive index differences as a function of time and calculates the polymer content of the cement and a molecular weight of the polymer. Connections from the micro computer means are shown by dashed lines.

The micro computer means is of the type well known to one of average skill in the art. It is programmed to direct the operations of the apparatus, to determine and record the flow times from the solution viscometer means, to record the refractive index difference as a function of time and to calculate from the refractive index difference the polymer current of the cement sample and from the flow times and said polymer content to calculate a molecular weight of the polymer. Conveniently, the micro computer is equipped with a recorder/display means to provide the data calculated.

In an operation of the apparatus and with reference to FIG. 1 using valve means shown in FIG. 2a, the dilution means of FIG. 3, the selector means of FIG. 4 and the solution viscometer means of FIG. 5, polymer cement from a polybutadiene manufacturing facility was subjected to the method of the invention and the polymer content and polymer molecular weight were determined. The preparation of the dilute polymer solution was as hereinbefore described and a constant volume of about 0.3 ml of cement was used to provide a constant volume of about 15.3 ml of dilute polymer solution, of which a constant volume of about 0.5 ml was supplied to the gel permeation chromatographic column and about 14.8 ml was supplied to the solution viscometer means. The hydrocarbyl solvent used was cyclohexane. From prior calibration of the gel permeation chromatographic column, the micro computer was programmed to calculate from the maximum refractive index difference the polymer content of the cement. From the flow times for both the solvent and the dilute polymer solution in the solution viscometer means and from the calculated polymer content of the cement, the micro computer was programmed to calculate a molecular weight of the polymer. Concentrations of from about 5 to about 20 weight percent of polybutadiene in the cement were determined with an accuracy of about ±1.5 percent and polybutadiene molecular weights above about 100,000 were readily determined. The micro computer may also be programmed to calculate other information about the polymer using the experimentally determined data. Such other information may include molecular weight distribution, number average and/or weight average molecular weight, polymer branching and viscosity in other solvents.

In further operations of an apparatus according to the invention and with reference to FIG. 6 using a valve means as shown in FIG. 2a, the dilution means of FIG. 3, the selector valve of FIG. 5 and the solution viscometer means of FIG. 5, cement from a polybutadiene manufacturing facility was used. The solvent in reservoir 103 was toluene and the solvent in reservoir 103a was cyclohexane. Accurate results were obtained for the polymer content of the cement and for the viscosity average molecular weight of the polymer.

What we claim is:

1. An apparatus for obtaining from a polymerization reactor a sample of polymer dissolved in one or more hydrocarbon diluents and for determining the polymer content of said sample and a molecular weight of said polymer, which apparatus comprises:
   (a) polymerization reactor means,
   (b) line for removing from said reactor means a polymeric product dissolved in one or more hydrocarbon polymerization diluents,
   (c) valve means for the removal from said line of an essentially constant volume sample of said polymeric product dissolved in said diluent,
   (d) means for storing hydrocarbyl solvent,
   (e) dilution means for adding hydrocarbyl solvent to and mixing said hydrocarbyl solvent with said essentially constant volume sample to provide an essentially constant volume of dilute polymer solution,
   (f) line for transferring said dilute polymer solution to a selector valve,
   (g) a first line from said selector valve for transferring a constant volume of said dilute polymer solution to a solution viscometer means which is maintained at an essentially constant temperature,
   (h) line for transferring hydrocarbyl solvent to said solution viscometer means,
   (i) a second line from said selector valve for transferring a constant volume of said dilute polymer solution to one or more gel permeation chromatographic columns,
   (j) line for transferring hydrocarbyl solvent to said gel permeation chromatographic columns,
   (k) means for causing said dilute polymer solution to flow through a capillary in said solution viscometer means and to activate a timing device to determine and record the flow time for the flow through said capillary of a constant volume of said dilute polymer solution,
   (l) means for causing said hydrocarbyl solvent to flow through a capillary in said solution viscometer means and to activate a timing device to determine and record the flow time for the flow through said capillary of a constant volume of said hydrocarbyl solvent,
   (m) means for causing the flow through said one or more gel permeation chromatographic columns of hydrocarbyl solvent at an essentially constant rate of flow,
   (n) means for determining and recording the refractive index difference as a function of time for the effluent from said one or more gel permeation chromatographic columns, said refractive index difference being the difference between the refractive index of the column effluent and that of a control fluid,
   (o) micro computer means programmed to control the operation of the apparatus, to determine and record said flow times from said solution viscometer means, to record said refractive index difference as a function of time and to calculate from said refractive index difference the polymer content of said sample and from said flow times and polymer content a molecular weight of said polymer, and
   (p) recorder/display means for providing the data calculated in (o).

2. An apparatus for obtaining from a polymerization reactor a sample of polymer dissolved in one or more hydrocarbon diluents and for determining the polymer content of said sample and a molecular weight of said polymer, which apparatus comprises:
   (a) polymerization reactor means,
   (b) line for removing from said reactor means a polymeric product dissolved in one or more hydrocarbon polymerization diluents,
   (c) valve means for the removal from said line of an essentially constant volume sample of said polymeric product dissolved in said diluent,
   (d) a first means for storing a first hydrocarbyl solvent,
   (e) a second means for storing a second hydrocarbyl solvent,
   (f) dilution means for adding and mixing said first hydrocarbyl solvent with said essentially constant volume sample to provide an essentially constant volume of dilute polymer solution, (g) line for transferring said dilute polymer solution to a selector valve, (h) a first line from said selector valve for transferring a constant volume of said dilute polymer solution to a solution viscometer means which is maintained at an essentially constant temperature, (i) a line for transferring said first hydrocarbyl solvent to said solution viscometer means, (j) a second line from said selector valve for transferring a constant volume of said dilute polymer solution to one or more gel permeation chromatographic columns, (k) a line for transferring said second hydrocarbyl solvent to said gel permeation chromatographic columns, (l) means for causing said dilute polymer solution to flow through a capillary in said solution viscometer means and to activate a timing device to determine and record the flow time for the flow through said capillary of a constant volume of said dilute polymer solution, (m) means for causing said first hydrocarbyl solvent to flow through said capillary in said solution viscometer means and to activate a timing device to determine and record the flow time for the flow through said capillary of a constant volume of said solvent, (n) means for causing the flow through said one or more gel permeation chromatographic columns of said second hydrocarbyl solvent at an essentially constant rate of flow, (o) means for determining and recording the refractive index difference as a function of time for the effluent from said one or more gel permeation chromatographic columns, said refractive index difference being the difference between the refractive index of the column effluent and that of a control fluid, (p) micro computer means programmed to control the operation of the apparatus, to determine and record said flow times from said solution viscometer means, to record said refractive index difference as a function of time and to calculate from said refractive index difference the polymer content of said sample and from said flow times and polymer content a molecular weight of said polymer, and (q) recorder/display means for providing data calculated in (p).

3. The apparatus of claim 1 or 2 wherein said valve means comprises a two-position valve having a housing equipped with ports, the chamber of said housing containing a movable two-position valve core equipped with flow channels each of which separately communicates with two adjacent ports, a first port being in communication with inlet means for polymer cement, a second port being in communication with outlet means for said cement, a third port being in communication with a dilution means, a fourth port being in communication with the dilute polymer solution in said dilution means and a fifth port being for removal of dilute polymer solution from the valve means, a first flow channel communicating in its first position with said first and second ports and in its second position with said second and third ports and a second flow channel communicating in its first position with said third and fourth ports and in its second position with said fourth and fifth ports.

4. The apparatus of claim 1 or 2 wherein said dilution means comprises a narrow diameter cylindrical chamber connected at its upper end to the third port of said valve means and connected at its lower end to a wide diameter closed cylindrical chamber which has at the side wall at its lower end a line in communication with the fourth port of said valve means and the solvent storage means and has at its upper end a line having a valve therein whereby said line may be connected to a supply of compressed gas or to the atmosphere, said narrow diameter cylindrical chamber having located concentrically therein and axially slidably movable within a close fitting plunger equipped with seals to prevent fluid leakage and having at its lower end depending into said wide diameter chamber a flange end for abutting engagement with the under surface of the wide diameter chamber at the point where the narrow diameter cylindrical chamber is attached to the wide diameter chamber, and said wide diameter closed cylindrical chamber having concentrically located therein and axially slidably movable within a close fitting double acting barrier piston equipped with seals to prevent fluid leakage and having a stirring means located within said wide diameter chamber and below said double acting barrier piston.

5. A method for determining for a sample of polymer dissolved in one or more hydrocarbon diluents and obtained from a polymerization reactor the polymer content and a molecular weight of said polymer, which method comprises:

(a) transferring an essentially constant volume of said sample to a dilution means and adding to and mixing with said sample a hydrocarbyl solvent to provide an essentially constant volume of dilute polymer solution, (b) transferring said dilute polymer solution to a selector valve, (c) transferring from said selector valve a constant volume of said dilute polymer solution to a solution viscometer means maintained at an essentially constant temperature, (d) transferring from said selector valve a constant volume of said dilute polymer solution to one or more gel permeation chromatographic columns, (e) causing said dilute polymer solution to flow through a capillary in said solution viscometer means and causing the activation of a timing device to determine and record the flow time for a constant volume of said dilute polymer solution to flow through said capillary, (f) transferring hydrocarbyl solvent to said solution viscometer means, causing said hydrocarbyl solvent to flow through said capillary and causing the activation of a timing device to determine and record the flow time for a constant volume of said hydrocarbyl solvent to flow through said capillary, (g) causing the flow through said one or more gel permeation chromatographic columns of hydrocarbyl solvent at an essentially constant rate of flow and causing the determining and recording of the refractive index difference as a function of time for the effluent from said one or more columns, said refractive index difference being the difference between the refractive index of the column effluent and that of a control fluid, (h) causing a micro computer means to direct the transfers and flows to take place, to determine and record the flow times through the capillary of the solution viscometer means, to record the refractive index difference as a function of time, to calculate from said refractive index difference the polymer content of said sample, to calculate from said polymer content and from said flow times a molecular weight of the polymer and to cause a recorder/display means to provide the data calculated.

6. A method for determining for a sample of polymer dissolved in one or more hydrocarbon diluents and obtained from a polymerization reactor the polymer content and a molecular weight of said polymer, which method comprises:

(a) transferring an essentially constant volume of said sample to a dilution means and adding to and mixing with said sample a first hydrocarbyl solvent to provide an essentially constant volume of dilute polymer solution, (b) transferring said dilute polymer solution to a selector valve, (c) transferring from said selector valve a constant volume of said dilute polymer solution to a solution viscometer means maintained at an essentially constant temperature, (d) transferring from said selector valve a constant volume of said dilute polymer solution to one or more gel permeation chromatographic columns, (e) causing said dilute polymer solution to flow through a capillary in said solution viscometer means and causing the activation of a timing device to determine and record the flow time for a constant volume of said dilute polymer solution through said capillary, (f) transferring said first hydrocarbyl solvent to said solution viscometer means, causing said solvent to flow through said capillary and causing the activation of a timing device to determine and record the flow time for a constant volume of said solvent to flow through said capillary, (g) causing the flow through said one or more gel permeation chromatographic columns of a second hydrocarbyl solvent at an essentially constant rate of flow and causing the determining and recording of the refractive index difference as a function of time for the effluent from said one or more columns, said refractive index difference being the difference between the refractive index of the column effluent and that of a control fluid, (h) causing a micro computer means to direct the transfers and flows to take place, to determine and record the flow times through the capillary of the solution viscometer means, to record the refractive index difference as a function of time, to calculate from said refractive index difference the polymer content of said sample, to calculate from said polymer content and from said flow times a molecular weight of the polymer and to cause a recorder/display means to provide the data calculated.

7. The method of claim 5 wherein said polymer is polybutadiene and said hydrocarbyl solvent is selected from benzene, toluene, cyclohexane and tetrahydrofuran.

8. The method of claim 6 wherein said polymer is polybutadiene, said first hydrocarbyl solvent is toluene and said second hydrocarbyl solvent is cyclohexane.

* * * * *